June 27, 1950 H. A. VERSCHUREN Plant Pat. 957
ROSE PLANT
Filed Oct. 18, 1948
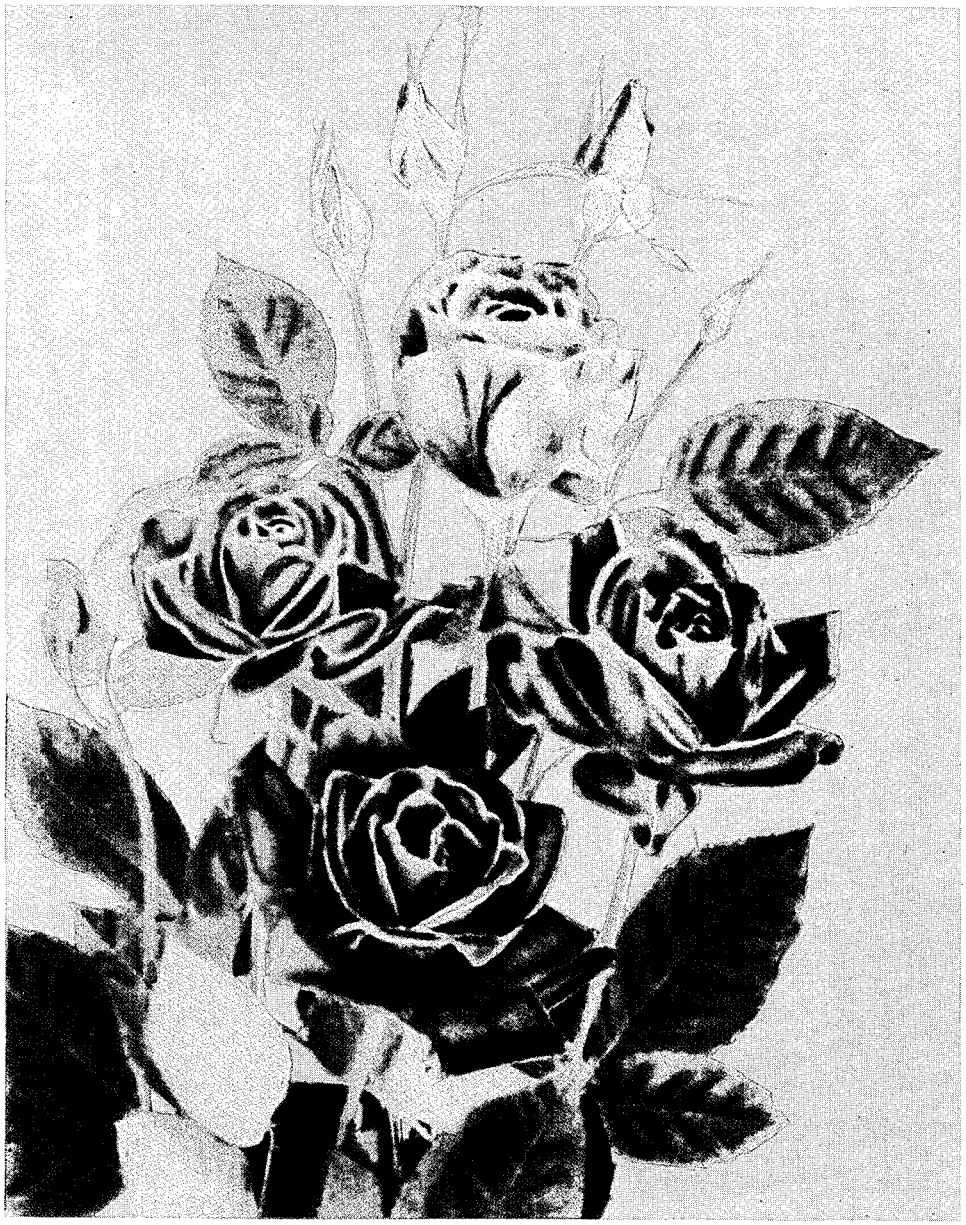
INVENTOR
HENDRIKUS ANTONIE VERSCHUREN, DECEASED,
Y MARIE THERESIA ANTIONETTA VERSCHUREN-HEYNEN, EXECUTRIX
By Orville M. Kile
Plant Pat. Agent Patented June 27, 1950

Plant Pat. 957

UNITED STATES PATENT OFFICE

957

ROSE PLANT

Hendrikus Antonie Verschuren, deceased, late of near Uden, Netherlands, by Marie Theresia Antionetta Verschuren-Heynen, executrix, near Uden, Netherlands, assignor to A. N. Pierson, Incorporated, Cromwell, Conn.

Application October 18, 1948, Serial No. 55,154

1 Claim. (Cl. 47—61)

The present invention relates to a new and distinct variety of hybrid tea rose plant. It originated from a cross between Better Times (Plant Patent 23) and Chieftain (Plant Patent 150) which was made by Hendrikus Antonie Verschuren at the Verschuren greenhouses in Haps, Holland.

The new variety is characterized particularly by its unique velvety color which ranges from approximately Oxblood in its bud stage, to Amaranth Purple or darker when fully open. This is combined with the pleasing manner in which the petals reflex in the fully open flower. Another distinctive characteristic is the compact, bushy and thorny growth of the plant.

Asexual reproduction of this new variety has shown its characteristics to be constant.

Illustrations accompanying these specifications show several blooms and buds of this new variety, together with portions of the stems and foliage, in approximately their true colors, as they were received one day after cutting and shipping. Allowance must be made for the fact that with the medium at hand the artist was unable to show the brilliance or velvety appearance which are so much a part of the beauty of the flower.

Following is a detailed description of this new variety of rose plant, color plate numbers referring to Ridgway's Color Standards and Nomenclature:

*The plant*

Form: More bushy than erect. Compact.

Blooming habit: Continuous.

Stems: Slender but strong. Approximately Cerro Green (Plate V). Thorns—many sharp horizontal thorns. Most of them are tinged with pink.

Foliage:

*Leaflets.*—3 to 5.

*Quantity.*—Abundant.

*Shape.*—Oval with acute to acuminate apex.

*Serrations.*—Edge sharply serrated.

*Size.*—Medium to large. Terminal leaflet measures 2½ to 3 inches long by 1½ to 2 inches wide. Lateral leaflets are much smaller.

*Color.*—Elm Green (Plate XVII).

*Texture.*—Leathery; smooth.

*Aspect.*—Upper surface, glossy. Under surface, dull.

*Rachis.*—Upper side, grooved and usually bronzed. Sharp hooked thorns found on under side.

*Stipules.*—Narrow and short; clinging.

*The flower*

Bud:

*Size.*—Medium; approximately 1½ inch long at cutting stage.

*Form.*—Conical; long-pointed.

*Color.*—Very dark red, almost Oxblood Red (Plate I).

*Sepals.*—Mostly simple; reflexing early. Biscay Green (Plate XVII).

*Calyx.*—Long and slender. Approximately Apple Green (Plate XVII).

*Peduncle.*—Sturdy; rather short; lighter green than stems and frequently bronzed. Holds flower erect and close to foliage.

*Opening.*—Slow and perfect.

Bloom:

*Size.*—Medium, fully opened flower measuring about 4½ inches in diameter.

*Borne.*—Singly on stems shorter than the usual greenhouse rose.

*Form.*—High-centered and symmetrical. Petals roll backward slightly as flower opens. When the flower is fully open the outer petals reflex backward toward the peduncle, while the intermediate and inner petals continue to stand upright, making somewhat of a ball formation.

*Petalage.*—Double, averaging about 26 petals in April. Although the petalage is not great, the flower has the appearance of a large and heavy rose, due partially to the substance and velvety appearance of the petals and partially to their arrangement.

*Color.*—General color effect of the open flower the first day after cutting is between Carmine and Oxblood Red (Plate I). The second day the color appears to be much lighter and more brilliant, and with more of the dark Rose tones shown in Plate XII than the Carmine tones of Plate I. The brilliance is particularly noticeable in artificial light and is therefore very valuable for decorative purposes at night. When fully open, the color of the two outer rows of petals takes on a purple glow, approximately Amaranth Purple (Plate XII), while the inner petals of many of the specimens remain the brighter, lighter tone. Many yellow stamens are visible in the open flower although usually they are partially hidden by some of the inner petals which remain folded. In a typical flower a creamy white streak runs up the center of the inner petals and this shows up as a small dot in the partially opened flower, due to the fact that the inner petals fold over in a "break," at that stage of opening.

Longevity: Flower opens slowly and lasts exceedingly well.

Petals:

*Texture.*—Substantial.

*Appearance.*—Inside very velvety. Outside silky.

*Shape.*—Outer petals are approximately round, with smooth edge. Intermediate petals are slightly wavy at edges.

*Arrangement.*—At first tightly imbricated, but later loose and informal although the flower remains symmetrical.

*Persistence.*—Petals drop off cleanly when old.

*Fragrance.*—Slight but very pleasing.

Reproductive organs:

*Pistils.*—Bunched. *Styles* dark red; *stigmas* cream color.

*Stamens.*—Many. Arranged in circle around pistils and at edge of pithy base rather than close to pistils.

Having thus disclosed the invention, it is claimed:

The new and distinct variety of hybrid tea rose plant, substantially as herein shown and described, characterized particularly by its unusually thorny and bushy growth; the velvety and brilliant aspect and the unique coloring of the flower from Carmine tones to Amaranth Purple tones in its different stages; combined with the distinctive form of the flower which varies in different stages of opening as described but remains high-centered and symmetrical throughout.

HENDRIKUS ANTONIE VERSCHUREN,
By MARIE THERESIA ANTIONETTA VERSCHUREN-HEYNEN,
*Executrix of Patent Rights of the Estate of Hendrikus Antonie Verschuren, Deceased.*

No references cited.